US012779169B2

(12) United States Patent
Ihara

(10) Patent No.: US 12,779,169 B2

(45) Date of Patent: Nov. 3, 2026

(54) MEDICAL TUBE AND CATHETER

(71) Applicant: ASAHI INTECC CO., LTD., Seto (JP)

(72) Inventor: Kosei Ihara, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 494 days.

(21) Appl. No.: 18/369,554

(22) Filed: Sep. 18, 2023

(65) Prior Publication Data

US 2024/0001074 A1 Jan. 4, 2024

Related U.S. Application Data

(63) Continuation of application No. PCT/JP2022/000381, filed on Jan. 7, 2022.

(51) Int. Cl.
*A61M 25/00* (2006.01)

(52) U.S. Cl.
CPC .... *A61M 25/0023* (2013.01); *A61M 25/0045* (2013.01)

(58) Field of Classification Search
CPC .......... A61M 25/0045; A61M 25/0012; A61M 25/005; A61M 2025/006; A61M 25/0054; A61M 25/0009; A61M 25/0043; A61M 2025/0059; A61M 25/0021; A61M 25/0023; A61M 25/0053; B29C 48/21
See application file for complete search history.

(56) References Cited

U.S. PATENT DOCUMENTS

| | | | | |
|---|---|---|---|---|
| 10,695,531 | B2 | 6/2020 | Suzuki | |
| 2016/0136387 | A1 | 5/2016 | Otake et al. | |
| 2017/0043119 | A1* | 2/2017 | Kubo | A61M 25/005 |
| 2018/0015254 | A1 | 1/2018 | Cragg et al. | |
| 2021/0308416 | A1* | 10/2021 | Ito | A61M 25/005 |

FOREIGN PATENT DOCUMENTS

| | | | |
|---|---|---|---|
| JP | 2004-097278 | A | 4/2004 |
| JP | 2014-236863 | A | 12/2014 |
| JP | 2018-143635 | A | 9/2018 |
| JP | 2020-171601 | A | 10/2020 |
| WO | 2004/022148 | A1 | 3/2004 |

* cited by examiner

*Primary Examiner* — Jason E Flick
(74) *Attorney, Agent, or Firm* — Oliff PLC

(57) ABSTRACT

A medical tube includes a tubular core layer and an outer layer arranged at an outer periphery of the core layer and having an outer peripheral surface substantially parallel to an axial direction of the medical tube. The core layer has a tubular inner core layer composed of a fluorine-based resin, and an outer core layer composed of a resin having a Young's modulus higher than that of the fluorine-based resin and arranged at an outer periphery of the inner core layer. The core layer has a specific configuration in which crest portions protruding toward a radially outer side of the medical tube and valley portions protruding toward a radially inner side of the medical tube are arranged repeatedly in the axial direction of the medical tube.

10 Claims, 5 Drawing Sheets

| | S1 (with the specific configuration SC) | S2 (without the specific configuration SC) | S3 (without the outer core layer 120) (without the specific configuration SC) |
|---|---|---|---|
| Average Young's modulus (MPa) | 40.5 | 54.2 | 30.3 |
| Average breaking load (N) | 6.9 | 6.9 | — |
| Average flexural modulus (MPa) | 73.9 | 136.2 | 48.2 |

FIG.5

MEDICAL TUBE AND CATHETER

This application is a bypass continuation of International Application No. PCT/JP2022/000381 filed Jan. 7, 2022, which is based upon and claims the benefit of priority from Japanese Patent Application No. 2021-067432 filed Apr. 13, 2021, the entire contents of the prior applications being incorporated herein by reference.

TECHNICAL FIELD

A technology disclosed herein relates to a medical tube and catheter.

BACKGROUND ART

A catheter is an elongated medical device to be inserted for use into tubular organs and body tissue of the human body, such as blood vessels, the digestive tract, and the ureter. The catheter may include, for example, a tubular hollow shaft, a distal tip joined to a distal end side of the hollow shaft, and a connector joined to a proximal end side of the hollow shaft. The hollow shaft may include, for example, a tubular core layer and an outer layer arranged at an outer periphery of the core layer. The core layer may be composed of a resin (for example, a fluorine-based resin) having excellent slidability and chemical resistance. The outer layer may be composed of a resin (for example, a polyamide-based resin) having excellent formability and flexibility.

The hollow shaft of a catheter needs to be highly flexible in order to avoid damaging the inner wall of a blood vessel and in order to improve vascular selectivity. Conventionally, a technology for adjusting the flexibility of a catheter is known in which an uneven structure having a plurality of protruding portions protruding toward a radially inward side and a depressed portion surrounding the plurality of protruding portions are provided in a core layer of a hollow shaft (for example, see Patent Document 1).

CITATION LIST

Patent Document

Patent Document 1: Japanese Patent Application Laid-Open No. 2014-236863

SUMMARY

Technical Problem

The present inventors focused on stretch resistance as a property required for a hollow shaft of a catheter in addition to the flexibility as described above. The term “stretch resistance” as used herein refers to a property of an article to resist a force of stretching the article, making it less stretchable. The present inventors found that if a hollow shaft has a low stretch resistance, a catheter may behave undesirably, resulting in decreased operativity of the catheter. For example, when the proximal end portion of the catheter is pulled toward the proximal side to withdraw the catheter from the body, the hollow shaft may be stretched, preventing the catheter from moving. When the proximal end portion is further pulled to the proximal side, the catheter may spring toward the proximal end side. Particularly in recent years, a hollow shaft having a thinner wall is required for reducing patient burden and for securing the dimension of a lumen through which a medical device such a guide wire is to be inserted. Consequently, the decrease in stretch resistance due to the thinner wall of the hollow shaft is likely to pose a problem.

In the above conventional technology, no consideration is given to the stretch resistance of the hollow shaft although it can improve the flexibility of the hollow shaft of the catheter. In other words, the above conventional technology has a problem in that the flexibility and stretch resistance of the hollow shaft of the catheter cannot be balanced at a high level. It is noted that such a problem is shared with not only hollow shafts of catheters but also medical tubes in general.

Disclosed herein is a technology which can solve the above problem.

Solution to Problem

The technology disclosed herein can be implemented, for example, according to the following aspects.

(1) A medical tube disclosed herein comprises a tubular core layer, and an outer layer composed of a resin and arranged at an outer periphery of the core layer and having an outer peripheral surface substantially parallel to an axis direction of the medical tube. The core layer has a tubular inner core layer composed of a fluorine-based resin, and an outer core layer composed of a resin having a Young’s modulus higher than that of the fluorine-based resin and arranged at an outer periphery of the inner core layer. The core layer has a specific configuration in which crest portions protruding toward a radially outward side of the medical tube and valley portions protruding toward a radially inward side of the medical tube are arranged repeatedly in the axis direction of the medical tube.

As described above, the present medical tube comprises the core layer having not only the inner core layer composed of a fluorine-based resin but also the outer core layer composed of a region having a Young’s modulus higher than that of the fluorine-based resin. This configuration confers high stretch resistance on the present medical tube. Moreover, the present medical tube comprises the core layer having the specific configuration in which the crest portions and the valley portions are arranged repeatedly. This configuration confers high flexibility on the present medical tube even though the core layer has the outer core layer. Therefore, the present medical tube enables the flexibility and stretch resistance of the present medical tube to be balanced at a high level. Furthermore, the present medical tube comprises the core layer having the specific configuration in which the crest portions and the valley portions are arranged repeatedly. This configuration can reduce a contact area between an inner peripheral portion of the medical tube and another medical device to be inserted into the medical tube. As a result, the medical device can smoothly move back and forth relative to the medical tube, leading to improved operativity.

(2) In the above medical tube, the specific configuration may comprise an intersecting portion where ridges of two of the crest portions aligned in the axis direction of the medical tube intersect to form a ridge of another of the crest portions. The present medical tube can improve the flexibility of the medical tube more effectively, and enables the flexibility and the stretch resistance of the medical tube to be balanced at an even higher level.

(3) In the above medical tube, the medical tube may have an outer diameter of 5 mm or less. The present medical tube can improve the flexibility of the medical tube by virtue of the presence of the specific configuration in the core layer even if the medical tube is difficult to manufacture due to its extremely small outer diameter.

(4) In the above medical tube, the core layer may be configured to have the specific configuration in a portion in the axis direction of the medical tube, but to not have the specific configuration in the remaining portion. The present medical tube can improve the flexibility of a portion where flexibility is particularly required in the medical tube while securing a high stretch resistance as a whole, conferring desired properties on the medical tube.

(5) In the above medical tube, the core layer may be configured to have the specific configuration in a portion including a distal end of the core layer, but not to have the specific configuration in the remaining portion. The present medical tube can improve the flexibility of a portion in a distal end side where flexibility is particularly required in the medical tube while securing a high stretch resistance as a whole.

(6) In the above medical tube, the outer core layer may have a thickness thinner than that of the inner core layer. The present medical tube can prevent decrease in the flexibility of the medical tube due to the presence of the outer core layer in the core layer, and enables the flexibility and stretch resistance of the medical tube to be balanced at an even higher level.

It is noted that the technology disclosed herein can be implemented according to various aspects, and can be implemented according to the aspects as, for example, elongated medical devices such as catheters comprising medical tubes, and methods of manufacturing those.

BRIEF DESCRIPTION OF THE DRAWINGS

FIG. 5 shows a diagram describing results from performance evaluation.

DETAILED DESCRIPTION OF EMBODIMENTS

A. Embodiments

A-1. Configuration of Catheter 10

Figure 1:
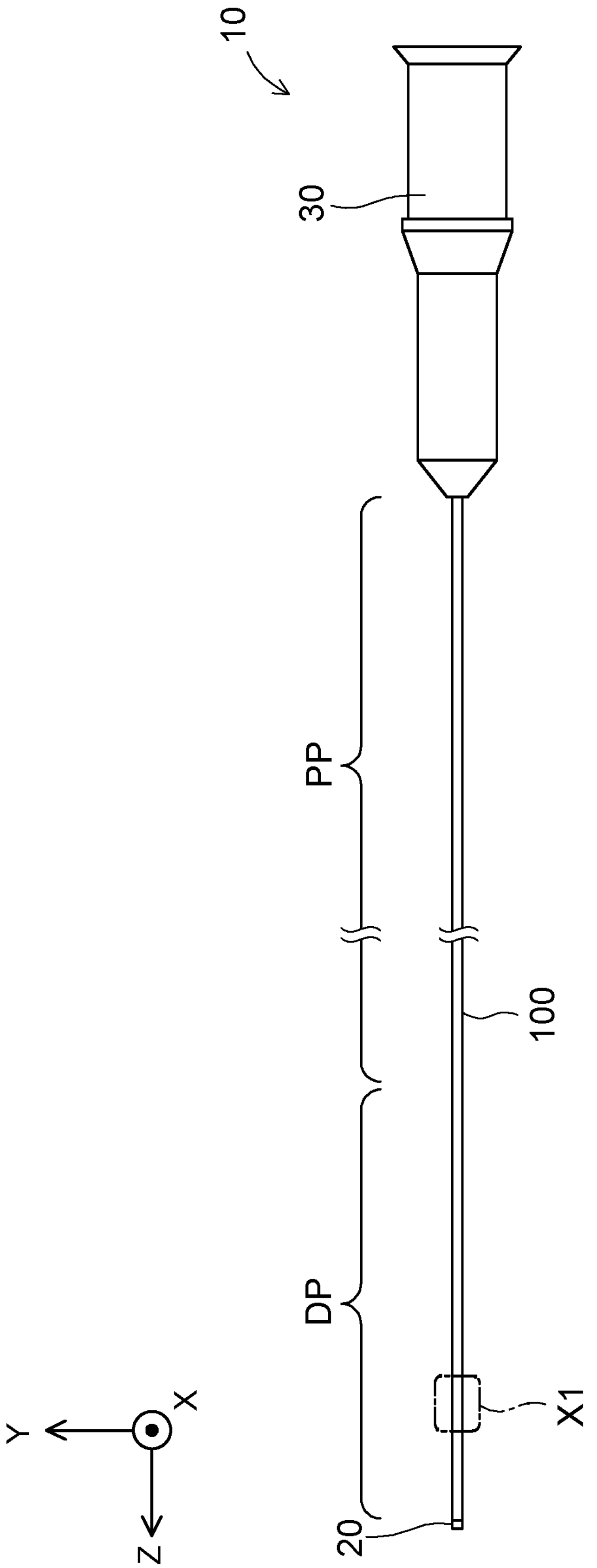
FIG. 1 shows a diagram schematically illustrating the configuration of a catheter 10 according to the present embodiment.

FIG. 1 shows a diagram schematically illustrating the configuration of a catheter 10 according to the present embodiment. The side view of the catheter 10 is shown in FIG. 1. It is noted that some features of the catheter 10 are not shown in FIG. 1 for convenience. In FIG. 1, the positive direction of the Z axis corresponds to a distal end side (distal side) to be inserted into the body, and the negative direction of the Z-axis corresponds to a proximal end side (near side) to be operated by an operator such as a medical practitioner. In FIG. 1, the catheter 10 as a whole is shown laid in a linear fashion parallel to the Z axis, but the catheter 10 is flexible enough to curve. It is noted that as used herein with reference to the catheter 10 and each component member thereof, a tip in the distal end side is referred to as a "distal end", the distal end and the vicinity thereof are referred to as a "distal end portion". A tip of the proximal end side is referred to as a "proximal end", and the proximal end and the vicinity thereof are referred to as a "proximal end portion".

The catheter 10 is an elongated medical device to be inserted for use into tubular organs and body issues in the human body such as blood vessels, the digestive tract, and the ureter. The overall length of the catheter 10 is, for example, about 1500 mm. The catheter 10 includes a hollow shaft 100, a flexible distal end tip 20 connected to a distal end portion of the hollow shaft 100, and a connector 30 connected to a proximal end portion of the hollow shaft 100. The hollow shaft 100 represents one example of medical tubes within the scope of the accompanying claims.

A-2. Configuration of Hollow Shaft 100

Figure 2:
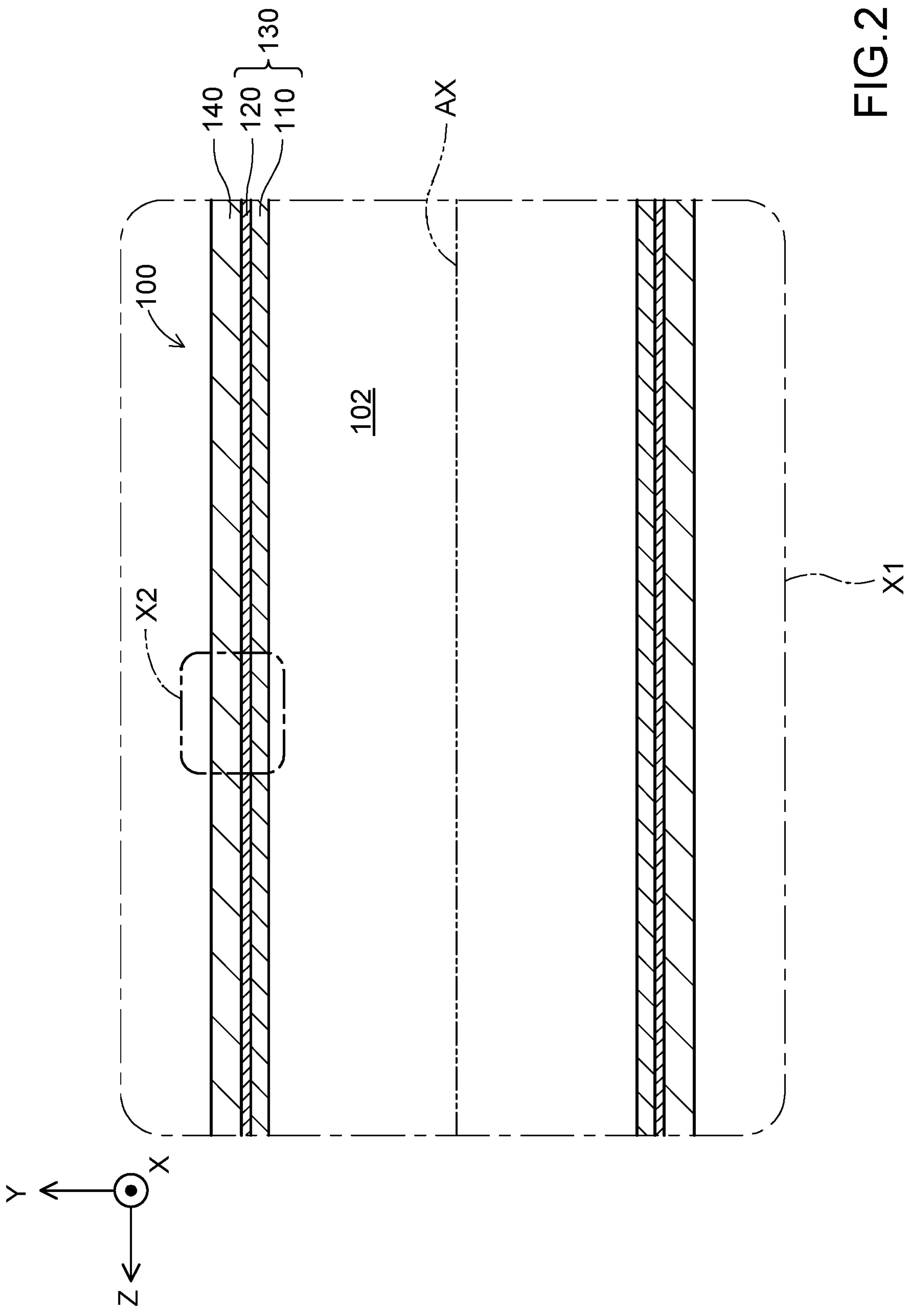
FIG. 2 shows a diagram schematically illustrating the detailed configuration of a hollow shaft 100.
Figure 3:
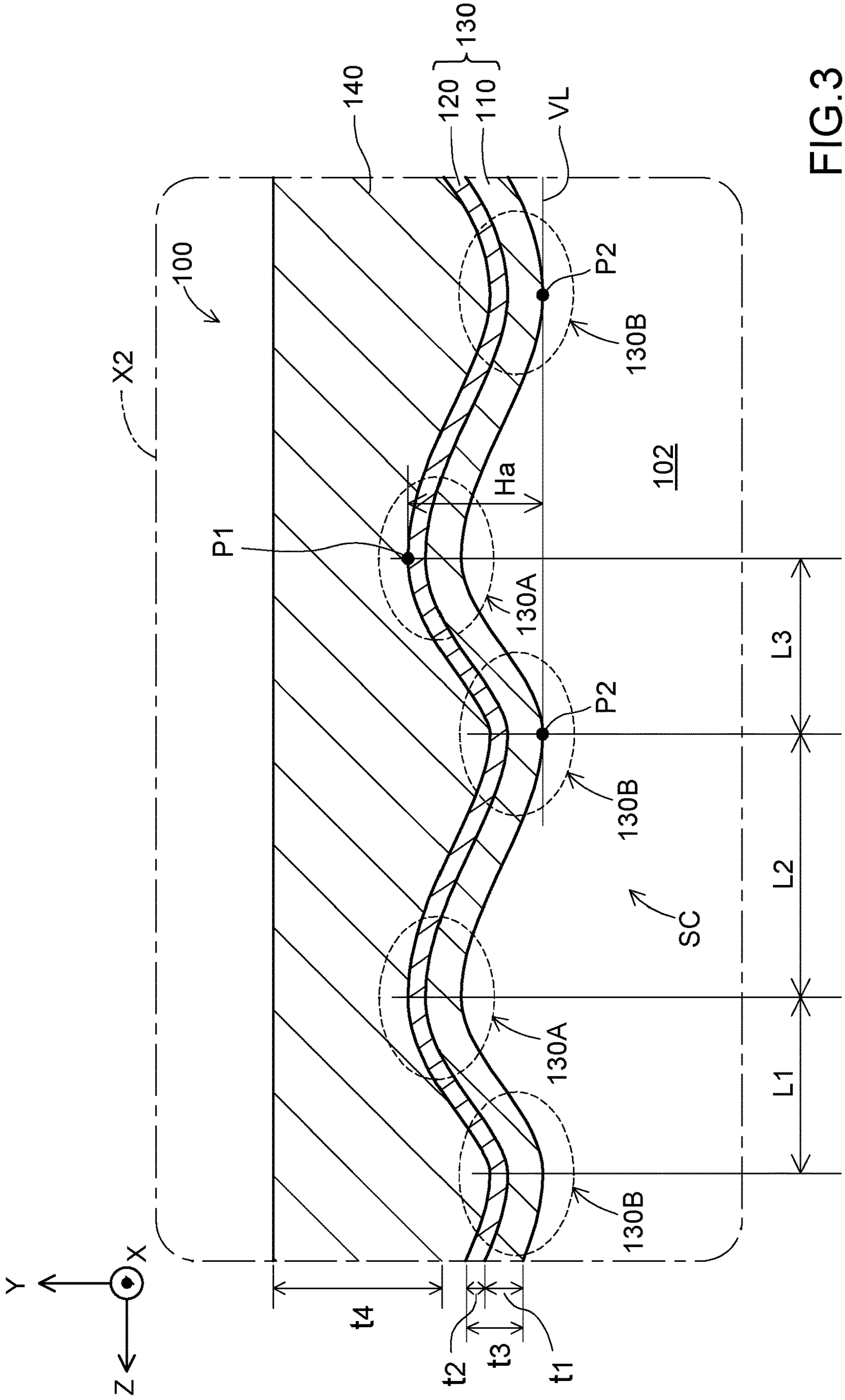
FIG. 3 shows a diagram schematically illustrating the detailed configuration of the hollow shaft 100.

FIG. 2 and FIG. 3 show diagrams illustrating the detailed configuration of the hollow shaft 100. FIG. 2 shows an enlarged view of the cross-sectional configuration of an X1 portion (the configuration of a cross section including a central axis AX of the hollow shaft 100) in FIG. 1. FIG. 3 shows an enlarged view of the cross-sectional configuration of an X2 portion (similarly, the configuration of a cross section including the central axis AX of the hollow shaft 100) in FIG. 2.

The hollow shaft 100 is a tubular (for example, cylindrical) member having openings each at the distal end and the proximal end. It is noted that the term "tubular (cylindrical)" as used herein refers to not only a perfect tubular shape (cylindrical shape) but also a substantially tubular shape as a whole (such as a substantially cylindrical shape, for example, a somewhat conical shape and a partly irregular shape). A hollow portion of the hollow shaft 100 serves as a lumen 102 into which a medical device such as a guide wire is to be inserted. In the present embodiment, the hollow shaft 100 has an outer diameter of 0.1 mm or more and 5.0 mm or less. It is noted that the hollow shaft 100 more preferably has an outer diameter of 0.5 mm or more and 3.0 mm or less.

The hollow shaft 100 includes a tubular core layer 130 and an outer layer 140 arranged at an outer periphery of the core layer 130. The outer layer 140 is arranged so as to cover the entire outer periphery of the core layer 130. In the present embodiment, the outer layer 140 is arranged so as to make contact with an outer peripheral surface of the core layer 130. It is noted that another member (for example, a reinforcing body such as a braid having multiple strands woven mutually) may exist between the outer layer 140 and the core layer 130.

The outer layer 140 has an outer peripheral surface substantially parallel to the axial direction (the Z axis direction) of the hollow shaft 100. In the present embodiment, the outer layer 140 corresponds to the outermost layer of the hollow shaft 100, and thus the hollow shaft 100 also has an outer peripheral surface substantially parallel to the axial direction of the hollow shaft 100.

The outer layer 140 is composed of a resin. As the resin composed of the outer layer 140, the followings may be used: for example, polyamide-based resins, polyester-based resins, polyurethane-based resins, polyolefin-based resins, aromatic polyether ketone-based resins, polycarbonate-based resins, and the like. These may be used alone or may be used in a combination of two or more. Polyamide-based resins can include polyamide and polyamide elastomers.

Polyurethane-based resins can include polyurethane and polyurethane elastomers. Polyester-based resins can include polybutylene terephthalate and polyester elastomers. Polyolefin-based resins can include polyethylene, polypropylene, and ethylene-propylene copolymers. Aromatic polyether ketone-based resins can include polyether ether ketone (PEEK). The outer layer 140 preferably contains and is composed of a polyamide-based resin or a polyurethane-based resin, and more preferably a polyamide-based resin in view of formability and flexibility. It is noted that the outer layer 140 may contain an optional component other than a polyamide-based resin and a polyurethane-based resin, but preferably contains 90% by mass or more of the polyamide-based resin and the polyurethane-based resin. More preferably, it contains 90% by mass or more of the polyamide-based resin. There are no particular limitations for the Young's modulus of a resin of which the outer layer 140 is composed, but it is preferably lower than the Young's modulus of, for example, a resin of which the outer core layer 120 described below is composed (a resin having a Young's modulus higher than that of a fluorine-based resin). The resin of which the outer layer 140 is composed preferably has a Young's modulus of less than 1.0 GPa in view of securing flexibility. The Young's modulus of the resin of which the outer layer 140 is composed can be determined by preparing a test piece in accordance with JIS K 7161 and subjecting it to measurement.

The thickness (the average thickness: hereinafter, the same applies to thickness unless otherwise noted) t4 of the outer layer 140 is preferably, for example, 10 μm or more, more preferably 15 μm or more, and even more preferably 30 μm or more in view of securing the stiffness of the hollow shaft 100. Further, the thickness t4 of the outer layer 140 is preferably, for example, 700 μm or less, more preferably 350 μm or less, and even more preferably 200 μm or less in view of preventing an excessively large thickness of the hollow shaft 100, and obtaining the hollow shaft 100 with a smaller outer diameter while securing the inner diameter of the lumen 102. In the present embodiment, the thickness t4 of the outer layer 140 is thicker than a thickness t3 of the core layer 130. However, the thickness t4 of the outer layer 140 may be thinner than the thickness t3 of the core layer 130. The thickness of a relatively thin portion in the outer layer 140 (a portion facing to a crest portion 130A described below) may be, for example, 5 μm or more and 100 μm or less, 15 μm or more and 80 μm or less, or 20 μm or more and 60 μm or less. The thickness of a relatively thick portion in the outer layer 140 (a portion facing to a valley portion 130B described below) may be, for example, 50 μm or more and 800 μm or less, 60 μm or more and 600 μm or less, or 70 μm or more and 400 μm or less.

The core layer 130 includes a tubular inner core layer 110 and an outer core layer 120 arranged at an outer periphery of the tubular inner core layer 110. That is, the hollow shaft 100 of the present embodiment is a three-layer tube in which the inner core layer 110 corresponds to the innermost layer, and the outer layer 140 corresponds to the outermost layer. The outer core layer 120 is arranged so as to cover the entire outer periphery of the inner core layer 110. In the present embodiment, the outer core layer 120 is arranged so as to make contact with an outer peripheral surface of the inner core layer 110.

The inner core layer 110 is composed of a fluorine-based resin, a resin having excellent slidability and chemical resistance. Here, the term "fluorine-based resin" collectively refers to fluorine-containing synthetic resins, including fluorine-containing thermoplastic resins, fluorine elastomers, and the like. Fluorine-based resins include, for example, PTFE (polytetrafluoroethylene), PFA (tetrafluoroethylene-perfluoroalkyl vinyl ether copolymer), or FEP (tetrafluoroethylene-hexafluoropropylene copolymer), ETFE (ethylene-tetrafluoroethylene copolymer), and the like. It is noted that the inner core layer 110 is composed of a fluorine-based resin when the inner core layer 110 may contain an optional component other than the fluorine-based resin, but contains 90% by mass or more of the fluorine-based resin.

The inner core layer 110 preferably has a thickness t1 of, for example, 3 μm or more, more preferably 5 μm or more, and even more preferably 7 μm or more in view of securing the slidability and the chemical resistance of an inner surface. Further, the thickness t1 of the inner core layer 110 is preferably, for example, 30 μm or less, more preferably 20 μm or less, and even more preferably 15 μm or less in view of preventing an excessively large thickness of the hollow shaft 100, and obtaining the hollow shaft 100 with a smaller outer diameter while securing the inner diameter of the lumen 102. The Young's modulus of a fluorine-based resin of which the inner core layer 110 is composed is preferably less than 1.0 GPa, more preferably 500 MPa or less. The Young's modulus of the fluorine-based resin of which the inner core layer 110 is composed may be 200 MPa or less. The Young's modulus of the resin of which the inner core layer 110 is composed can be measured in accordance with JIS K 7161.

The outer core layer 120 is composed of a resin having a Young's modulus higher than that of a fluorine-based resin (hereinafter referred to as a "high Young's-modulus resin"). The high Young's-modulus resin of which the outer core layer 120 is composed preferably has a Young's modulus of, for example, 1.0 GPa or more. High Young's-modulus resins include, for example, polyimide-based resins, aromatic polyether ketone-based resins such as PEEK, and high Young's modulus polyamide-based resins such as TR55. Polyimide-based resins are macromolecules having imide bonds in the main chains, and include polyimide, polyamideimide, polyester imide, polyetherimide, and the like. These resins are usually used alone, but may be used in a mixture of two or more. Among polyimide-based resins, polyimide having excellent mechanical properties in particular is preferably used, and among polyimide, aromatic polyimide is further preferably used. This aromatic polyimide may be thermoplastic or may be non-thermoplastic. It is noted that the outer core layer 120 is composed of a high Young's-modulus resin when the outer core layer 120 may contain an optional component other than the high Young's-modulus resin, but contains 90% by mass or more of the high Young's-modulus resin. A resin of which the outer core layer 120 is composed is preferably a resin having a Young's modulus higher than that of a resin of which the outer layer 140 is composed. The high Young's-modulus resin more preferably has a Young's modulus of 1.5 GPa or more, even more preferably 2.0 GPa or more. The high Young's-modulus resin may preferably have a Young's-modulus of 2.5 GPa or more. The Young's modulus of the high Young's-modulus resin can be measured in accordance with JIS K 7161.

The outer core layer 120 is a layer added to a configuration of a hollow shaft for a conventional catheter, i.e., a two-layer configuration having a core layer composed of a fluorine-based resin and an outer layer arranged at an outer periphery of the core layer, in order to improve stretch resistance. The outer core layer 120 preferably has a thickness t2 of, for example, 0.5 μm or more, more preferably 1.5 μm or more, and even more preferably 3 μm or more in view of effectively increasing the stretch resistance of the hollow shaft 100. Further the outer core layer 120 preferably has a thickness t2 of, for example, 30 μm or less, more preferably 15 μm or less, and even more preferably 10 μm or less in view of preventing reduced flexibility of the hollow shaft 100 due to the presence of the outer core layer 120, and in view of facilitating formation of a specific configuration SC described below. From the same perspective, the thickness t2 of the outer core layer 120 is preferably thinner than the thickness t1 of the inner core layer 110.

A-3. Detailed Configuration of Core Layer 130

Next, the detailed configuration of the core layer 130 will be described. As shown in FIG. 3, the core layer 130 has a configuration (hereinafter referred to as the "specific configuration Sc") in which the crest portions 130A protruding toward a radially outward side of the hollow shaft 100 (in other words, protruding toward the outer layer 140) and the valley portions 130B protruding toward radially inward side of the hollow shaft 100 (in other words, protruding toward the lumen 102) are arranged repeatedly in the axial direction (the Z axis direction) of the hollow shaft 100. In other words, the specific configuration SC of the core layer 130 has a configuration in which the core layer 130 has a corrugated shape in a cross-section including the central axis AX of the hollow shaft 100 (see FIG. 2). A pitch of forming the crest portions 130A may be, for example, 0.01 mm to 3.0 mm. A height Ha of a crest portion 130A may be, for example, 0.01 mm to 2.0 mm. It is noted that the height Ha of the crest portion 130A is defined as a distance from an apex P1 of the crest portion 130A to a hypothetical line VL connecting bottom points P2 of two of the valley portions 130B sandwiching the crest portion 130A. The crest portions 130A are portions where corresponding portions of the core layer 130 are mountain-folded and can also be expressed as "mountain-folded portions" while the valley portions 130B are portions where corresponding portions of the core layer 130 are valley-folded and can also be expressed as "valley-folded portions". It is noted that the specific configuration SC is omitted in FIG. 2.

Figure 4:
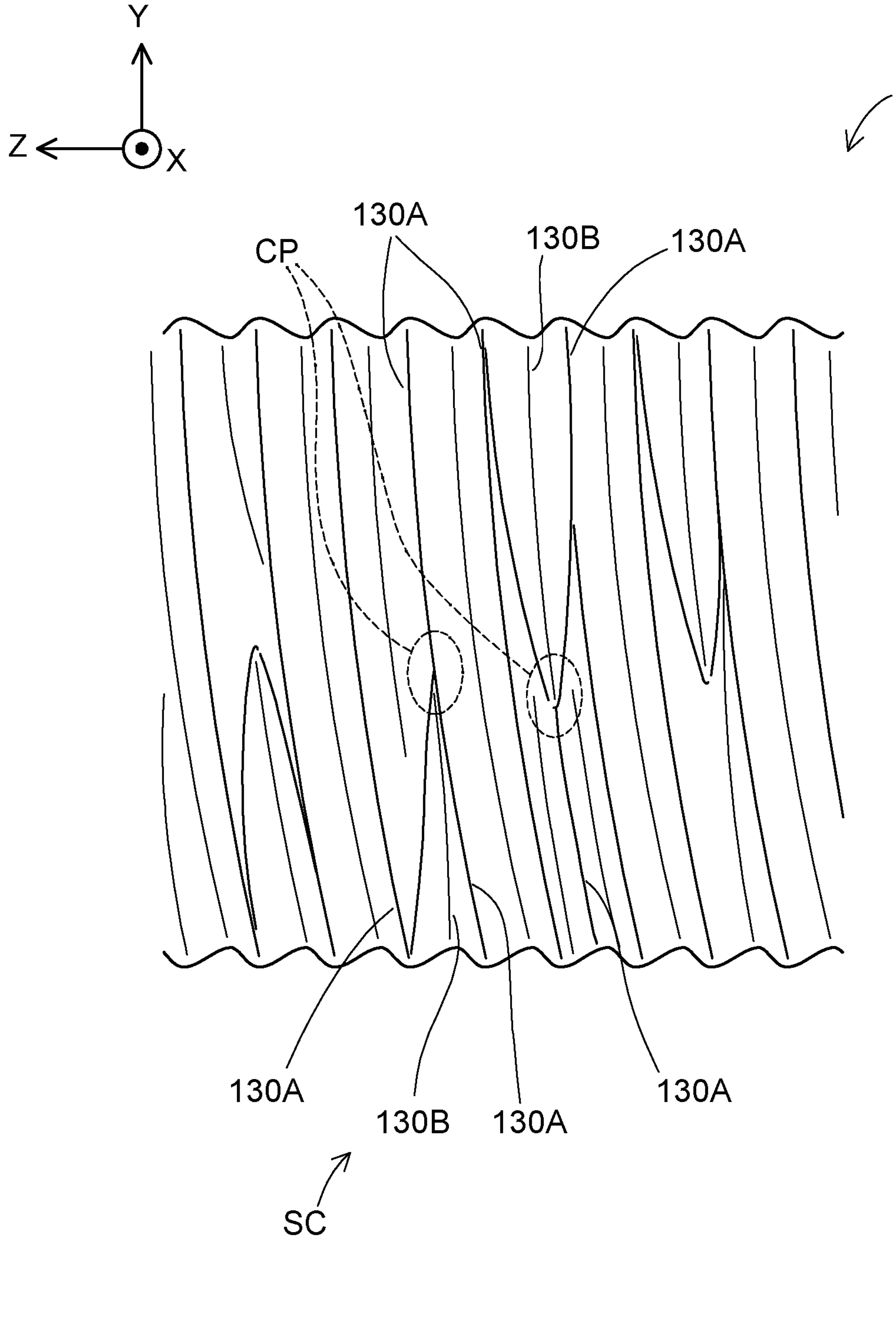
FIG. 4 shows a diagram schematically illustrating the appearance of a core layer 130 having a specific configuration SC.

FIG. 4 shows a diagram schematically illustrating the appearance of the core layer 130 having the specific configuration SC. As shown in FIG. 4, the crest portions 130A and the valley portions 130B of the specific configuration SC may be formed throughout the entire circumference of the core layer 130. However, in the present embodiment, only a portion of the core layer 130, specifically, only a portion of the core layer 130 that includes a distal end (a portion corresponding to a distal portion DP of the hollow shaft 100 shown in FIG. 1) has the specific configuration SC while the remaining portion of the core layer 130 (corresponding a proximal portion PP of the hollow shaft 100 shown in FIG. 1) does not have the specific configuration SC. In the present embodiment of the hollow shaft 100, a portion of the core layer 130 corresponding to the distal portion DP of the hollow shaft 100 has the specific configuration SC. This configuration can improve the flexibility of the distal portion DP of the hollow shaft 100.

As shown in FIG. 4, the specific configuration SC of the core layer 130 includes an intersecting portion CP where the ridges of two of the crest portions 130A aligned in the axial direction (the Z-axis direction) of the hollow shaft 100 intersect to form a ridge of another of the crest portions 130A. In other words, the specific configuration SC of the core layer 130 represents a configuration in which unevenness is also present in the circumferential direction of the hollow shaft 100 (the core layer 130). It is noted that examples of shapes having the intersecting portion CP where the ridges of two of the crest portions 130A aligned in the axial direction of the hollow shaft 100 intersect to form a ridge of another of the crest portions 130A include the Miura fold and the Yoshimura pattern.

As shown in FIG. 3 in the present embodiment, the apexes of the crest portions 130A are eccentric in the axial direction (the Z-axis direction) of the hollow shaft 100. That is, with reference to one of the crest portions 130A and two of the valley portions 130B sandwiching the one of the crest portions 130A, a distance L1 as a distance from the bottom point of one of the two valley portions 130B to the apex of the one of the crest portions 130A (a distance along the axial direction of the hollow shaft 100; the same applies hereinafter) is shorter than a distance L2 from the bottom point of the other of the two of the valley portions 130B to the apex of the one of the crest portions 130A. However, the distance L2 may be the same as the distance L1. It is noted that the distance L1 and the distance L2 may satisfy the relationship $0.5 \leq L1/L2 \leq 1.0$, or may satisfy the relationship $0.6 < L1/L2 \leq 0.9$, or may satisfy the relationship $0.7 \leq L1/L2 \leq 0.8$. Similarly, in the present embodiment, the bottom points of the valley portions 130B are eccentric in the axial direction of the hollow shaft 100. That is, with reference to one of the valley portions 130B and two of the crest portions 130A sandwiching the one of the valley portions 130B, the distance L2 as a distance from the apex of one of the two crest portions 130A to the bottom point of the one of the valley portions 130B is shorter than a distance L3 from the apex of the other of the two crest portions 130A to the bottom point of the one of the valley portions 130B. However, the distance L2 may be the same as the distance L3. It is noted that the distance L2 and the distance L3 may satisfy the relationship $0.5 \leq L3/L2 \leq 1.0$, or may satisfy the relationship $0.6 \leq L3/L2 \leq 0.9$, or may satisfy the relationship $0.7 \leq L3/L2 \leq 0.8$.

A-4. Method of Manufacturing Hollow Shaft 100

Next, an example of a method of manufacturing the hollow shaft 100 will be described. First, the inner core layer 110 is formed around a cored bar. Next, the inner core layer 110 formed around the cored bar is immersed into a liquid containing a material for forming the outer core layer 120, and then pulled out of the liquid. The outer core layer 120 is then formed by baking the material for forming the outer core layer 120 adhered around the inner core layer 110. In this way, the core layer 130 is formed around the cored bar, including the inner core layer 110 and the outer core layer 120.

Next, the specific configuration SC is formed at the core layer 130. Specifically, one end of a portion at which the specific configuration SC is to be formed in the core layer 130 is fixed, and the other end is then pushed toward the side of the one end. Then the other end is pulled back to form the specific configuration SC in the core layer 130 in which the crest portions 130A and the valley portions 130B are repeated in the axial direction.

Next, the hollow shaft 100 including the core layer 130 and the outer layer 140 is formed around the cored bar by forming the outer layer 140 at the outer periphery of the core layer 130 formed around the cored bar. Finally, the cored bar is withdrawn. The hollow shaft 100 can be manufactured, for example, by the aforementioned manufacturing method.

A-5. Performance Evaluation

Performance evaluation was performed with respect to the stretch resistance and flexibility of the hollow shaft. FIG. 5 shows a diagram describing the results from the performance evaluation.

As shown in FIG. 5, performance evaluation was performed using 3 samples (S1 to S3) of hollow shafts. The sample S1 is from the example of the hollow shaft 100 of the present embodiment as described above. That is, the sample S1 is a three-layer tube including: the core layer 130 including the inner core layer 110 and the outer core layer 120; and the outer layer 140, in which the core layer 130 has the specific configuration SC (a configuration in which the crest portions 130A and the valley portions 130B are repeated in the axial direction). It is noted that PTFE was used as a material for forming the inner core layer 110, and polyimide was used as a material for forming the outer core layer 120, and polyamide elastomer (pebax35 from ARKEMA) was used as a material for forming the outer layer 140. The thickness of the inner core layer 110 was set to about 10 μm, and the thickness of the outer core layer 120 was set to about 3 μm, and the thickness of the outer layer 140 was set to about 40 μm in a relatively thin portion (facing the crest portion 130A) and about 80 μm in a relatively thick portion (facing the valley portion 130B).

The samples S2 and S3 are Comparative Examples. That is, the sample S2 is a three-layer tube similar to the sample S1, but has the core layer 130 without the specific configuration SC. That is, the inner core layer 110 and outer core layer 120 of the core layer 130 in the sample S2 are each configured to have an outer peripheral surface substantially parallel to the axial direction of the hollow shaft. The sample S3 is a two-layer tube including: the core layer 130 consisting only of the inner core layer 110; and the outer layer 140. That is, the sample S3 does not have the outer core layer 120 composed of a resin having a Young's modulus higher than that of a fluorine-based resin. In the sample S3, the core layer 130 does not have the specific configuration SC. That is, the inner core layer 110 of the core layer 130 in the sample S3 is configured to have an outer peripheral surface substantially parallel to the axial direction of the hollow shaft. It is noted that a material for forming each layer of the samples S2, S3 and the thickness thereof are similar to those of the sample S1.

The average values of Young's modulus, breaking load, and flexural modulus were measured and determined at N=5 for each sample by a method according to JIS K 7161-2014, JIS K 7171. The higher the average Young's modulus, the higher is the stretch resistance of the hollow shaft, and the lower the average flexural modulus, the higher is the flexibility. It is noted that the average breaking load of the sample S3 was not measured.

The value of the average Young's modulus for the sample S1 was lower than that of the sample S2 which did not have the specific configuration SC, but sufficiently higher than that of the sample S3 which did not have the outer core layer 120. This demonstrates that the sample S1 has sufficiently high stretch resistance. It is assumed that that the Young's modulus of the sample Si having the outer core layer 120 was sufficiently high because the outer core layer 120 was composed of a high Young's-modulus resin. It is noted that the value of the average breaking load for the sample S1 was comparable to that of the sample S2 which did not have the specific configuration SC. This suggests that the presence or absence of the specific configuration SC has little impact on the breaking load.

The value average of flexural modulus for the sample S1 was higher than that of the sample S3 which did not have the outer core layer 120, but sufficiently lower than that of the sample S2 which did not have the specific configuration SC. This demonstrates that the sample S1 has sufficiently high flexibility. It is assumed that the specific configuration SC in which the crest portions 130A and the valley portions 130B are repeated in the axial direction, which was designed for improving flexibility, sufficiently lowered the flexural modulus of the sample S1 having the specific configuration SC.

These results from the performance evaluation as described above demonstrate that the hollow shaft 100 having the core layer 130 and the outer layer 140 can balance between the flexibility and stretch resistance of the hollow shaft 100 at a high level, wherein the core layer 130 has the inner core layer 110 composed of a fluorine-based resin and the outer core layer 120 composed of a resin having a Young's modulus higher than that of the fluorine-based resin, and the core layer 130 has the specific configuration SC in which the crest portions 130A and the valley portions 130B are repeated in the axial direction.

A-6. Effect of the Present Embodiment

As described above, the hollow shaft 100 of the catheter 10 according to the present embodiment has the tubular core layer 130, and the outer layer 140 composed of a resin and arranged around the outer periphery of the core layer 130 and having an outer surface substantially parallel to the axial direction of the hollow shaft 100. The core layer 130 has the tubular inner core layer 110 composed of a fluorine-based resin, and the outer core layer 120 composed of a resin having a Young's modulus higher than that of fluorine-based resin and arranged around the outer periphery of the inner core layer 110. The core layer 130 has the specific configuration SC in which the crest portions 130A protruding toward the radially outward side of the hollow shaft 100 and the valley portions 130B protruding toward the radially inward side of the hollow shaft 100 are arranged repeatedly in the axial direction of the hollow shaft 100.

As described above, the hollow shaft 100 according to the present embodiment has high stretch resistance because in addition to the inner core layer 110 composed of a fluorine-based resin, the core layer 130 has the outer core layer 120 composed of a resin having a Young's modulus higher than that of the fluorine-based resin. The hollow shaft 100 according to the present embodiment has high flexibility even though the core layer 130 has the outer core layer 120. This is because the core layer 130 has the specific configuration SC in which the crest portions 130A and the valley portions 130B are arranged repeatedly. Therefore, the flexibility and stretch resistance of the hollow shaft 100 can be balanced at a high level according to the hollow shaft 100 of the present embodiment.

In the hollow shaft 100 according to the present embodiment, the specific configuration SC of the core layer 130 includes the intersecting portion CP where the ridges of two of the crest portions 130A aligned in the axial direction of the hollow shaft 100 intersect to form another of the crest portions 130A. Therefore, the flexibility of the hollow shaft 100 can be improved even more effectively, and the flexibility and stretch resistance of the hollow shaft 100 can be balanced at an even higher level according to the hollow shaft 100 of the present embodiment.

It is noted that the hollow shaft 100 according to the present embodiment has an outer diameter of 5 mm or less. Thus, even in the hollow shaft 100 which is difficult to be processed due to its extremely small outer diameter, the flexibility of the hollow shaft 100 can be improved by forming the specific configuration SC in the core layer 130 according to the method as described above.

In the hollow shaft 100 according to the present embodiment, the core layer 130 has the specific configuration SC in a portion in the axial direction of the hollow shaft 100, and does not have the specific configuration SC in the remaining portion. Therefore, the hollow shaft 100 according to the present embodiment can improve the flexibility of a portion where flexibility is particularly required while securing high stretch resistance as a whole, conferring desired properties on the hollow shaft 100. More specifically, in the hollow shaft 100 according to the present embodiment, the core layer 130 has the specific configuration SC in a portion including the distal end of the core layer 130, and does not have the specific configuration SC in the remaining portion. Therefore, the hollow shaft 100 according the present embodiment can improve the flexibility of a portion in the distal end side where flexibility is particularly required while securing high stretch resistance as a whole.

In the hollow shaft 100 according to the present embodiment, the thickness t2 of the outer core layer 120 is thinner than the thickness t1 of the inner core layer 110. Therefore, the hollow shaft 100 according to the present embodiment can prevent decrease in the flexibility of the hollow shaft 100, which otherwise may result from the presence of the outer core layer 120 in the core layer 130, and enables the flexibility and stretch resistance of the hollow shaft 100 to be balanced at an even higher level.

Moreover, the catheter 10 according to the present embodiment, which includes the hollow shaft 100 configured as described above, enables the flexibility and stretch resistance of the hollow shaft 100 of the catheter 10 to be balanced at a high level.

B. MODIFIED EXAMPLES

The technology disclosed herein is not limited to those embodiments as described above, and can be modified to various forms without departing from the spirit of the present disclosure. For example, the following modifications are possible.

The configuration of the catheter 10 in the above embodiment is merely illustrative, and can be modified in various ways. For example, in the above embodiment, the hollow shaft 100 of the catheter 10 consists of the core layer 130 and the outer layer 140, but may further include a second outer layer arranged around the outer periphery of the outer layer 140. In such a configuration, another member (for example, a reinforcing body such as a braid having multiple strands woven mutually) may exist between the outer layer 140 and the second outer layer.

In the above embodiments, the core layer 130 consists of the inner core layer 110 and the outer core layer 120, but the core layer 130 may further includes an additional layer. The additional layer may be arranged at the inner periphery of the inner core layer 110, or may be arranged between the inner core layer 110 and the outer core layer 120, or may be arranged at the outer periphery of the outer core layer 120.

In the above embodiment, only a portion of the core layer 130 which includes the distal end (the distal portion DP of the hollow shaft 100) has the specific configuration SC, but the portion of the core layer 130 having the specific configuration SC can be changed according to the desired properties of the hollow shaft 100. The core layer 130 may have the specific configuration SC throughout the entire length thereof.

In the above embodiment, the specific configuration SC of the core layer 130 includes the intersecting portion CP where the ridges of two of the crest portions 130A aligned in the axial direction of the hollow shaft 100 intersect to form another of the crest portions 130A, but the specific configuration SC does not necessarily need to include the intersecting portion CP.

The thicknesses of component members of the hollow shaft 100 and the relationship between the thicknesses of the members in the above embodiment are merely illustrative, and can be modified in various ways. Moreover, the materials of component members of the hollow shaft 100 in the above embodiment are merely illustrative, and other materials may also be used. Furthermore, the method of manufacturing the hollow shaft 100 in the above embodiment is merely illustrative, and other manufacturing methods may be used.

In the above embodiment, the hollow shaft 100 of the catheter 10 is described as an example of a medical tube, but the technology disclosed herein is equally applicable to other medical tubes (for example, a hollow shaft of a balloon catheter, a tube for an indwelling needle, and the like).

DESCRIPTION OF SYMBOLS

10: Catheter
20: Distal tip
30: Connector
100: Hollow shaft
102: Lumen
110: Inner core layer
120: outer core layer
130: Core layer
130A: Crest portion
130B: Valley portion
140: Outer layer
CP: intersecting portion
DP: Distal portion
PP: Proximal portion
SC: Specific Configuration

The invention claimed is:

1. A medical tube comprising:
a tubular core layer; and
an outer layer that is composed of a resin, is arranged at an outer periphery of the core layer, and has an outer peripheral surface substantially parallel to an axial direction of the medical tube, wherein
the core layer includes:
a tubular inner core layer composed of a fluorine-based resin, and
an outer core layer composed of a resin having a Young's modulus higher than a Young's modulus of the fluorine-based resin, the outer core layer being arranged at an outer periphery of the inner core layer, the core layer has a specific configuration in which crest portions protruding toward a radially outer side of the medical tube and valley portions protruding toward a radially inner side of the medical tube are arranged repeatedly in the axial direction of the medical tube, and the specific configuration includes an intersecting portion where ridges of two of the crest portions aligned in the axial direction of the medical tube intersect to form a ridge of another of the crest portions.

2. The medical tube according to claim 1, wherein the medical tube has an outer diameter of 5 mm or less.

3. The medical tube according to claim 1, wherein the core layer has the specific configuration in a portion in the axial direction of the medical tube, and does not have the specific configuration in a remaining portion of the core layer.

4. The medical tube according to claim 3, wherein the core layer has the specific configuration in the portion including a distal end of the core layer, and does not have the specific configuration in the remaining portion.

5. The medical tube according to claim 1, wherein the outer core layer has a thickness less than a thickness of the inner core layer.

6. A catheter comprising the medical tube according to claim 1.

7. The medical tube according to claim 1, wherein the crest portions and the valley portions are provided along an entire circumference of the core layer.

8. The medical tube according to claim 1, wherein the crest portions and the valley portions are arranged in an alternating manner in the axial direction of the medical tube.

9. The medical tube according to claim 1, wherein a first distance between a first crest portion and an adjacent first valley portion is different from a second distance between the first crest portion and an adjacent second valley portion.

10. The medical tube according to claim 1, wherein a first distance between a first crest portion and an adjacent first valley portion is the same as a second distance between the first crest portion and an adjacent second valley portion.

* * * * *